United States Patent [19]
Login et al.

[11] Patent Number: 5,190,749
[45] Date of Patent: * Mar. 2, 1993

[54] COPOLYMERS OF VINYL PYRROLIDONE AND A QUATERNARY AMMONIUM MONOMER COMPLEXED WITH $H_2O_2$ IN THE FORM OF FREE-FLOWING POWDERS

[75] Inventors: Robert B. Login, Oakland; John J. Merianos, Middletown, both of N.J.

[73] Assignee: ISP Investments Inc., Wilmington, Del.

[*] Notice: The portion of the term of this patent subsequent to Dec. 31, 2008 has been disclaimed.

[21] Appl. No.: 820,178

[22] Filed: Jan. 13, 1992

[51] Int. Cl.$^5$ .................. A61K 31/79; A61K 31/785
[52] U.S. Cl. .................. 424/78.24; 424/616; 514/772.5
[58] Field of Search .................. 514/772.5; 424/616, 424/78.08, 78.24

[56] References Cited

U.S. PATENT DOCUMENTS

| | | | |
|---|---|---|---|
| 3,376,110 | 4/1968 | Shiraeff | 524/548 |
| 4,801,460 | 1/1989 | Goertz et al. | 514/772.5 |
| 5,008,093 | 4/1991 | Merianos | 524/438 |
| 5,066,488 | 11/1991 | Merianos et al. | 424/486 |
| 5,077,047 | 12/1991 | Biss et al. | 424/405 |

FOREIGN PATENT DOCUMENTS 3444552 12/1986 Fed. Rep. of Germany.

Primary Examiner—Thurman K. Page
Assistant Examiner—Peter F. Kulkosky
Attorney, Agent, or Firm—Walter Katz; Marilyn J. Maue; Joshua J. Ward

[57] ABSTRACT

Copolymers of vinyl pyrrolidone and a quaternary ammonium monomer complexed with $H_2O_2$ in the form of free-flowing powders is described. The products are made in a fluidized bed of said copolymer maintained at a reaction temperature of from room temperature to about 60° C. The fluidized bed is contacted with finely divided droplets of a 30 to 85% by weight aqueous $H_2O_2$ solution at a feed rate of about 1-10 g/minute/kg copolymer present. The copolymer-$H_2O_2$ product preferably contains about 10-20% $H_2O_2$ (1:1 molar ratio), and less than about 5% water. The product can be used as a hair bleach enhancer which provides dual hair conditioning properties.

11 Claims, No Drawings

COPOLYMERS OF VINYL PYRROLIDONE AND A QUATERNARY AMMONIUM MONOMER COMPLEXED WITH $H_2O_2$ IN THE FORM OF FREE-FLOWING POWDERS

FIELD OF THE INVENTION

This invention relates to copolymers of vinyl pyrrolidone and a quaternary ammonium monomer complexed with hydrogen peroxide, and more particularly, to a fluidized bed process for the production of such products in the form of free-flowing powders.

DESCRIPTION OF THE PRIOR ART

Stabilized $H_2O_2$ compositions have found wide utility in commercial and industrial applications, e.g. as antiseptics, disinfectants, sterilization agents, bleaching materials, washing concentrates, etchants, in cosmetic preparations, and as a catalyst in polymerizations requiring a free radical source. In biological applications which require an antiseptic, disinfectant or sterilization agent, such $H_2O_2$ compositions require release of an effective amount of oxygen at a desired rate.

Shiraeff U.S. Pat. Nos. 3,376,110 and 3,480,557, disclosed that a solid, stabilized hydrogen peroxide composition of hydrogen peroxide and a polymeric N-vinyl heterocyclic compound could be prepared from an aqueous solution of the components. The process involved mixing PVP and a substantial excess of aqueous $H_2O_2$ and evaporating the solution to dryness. The $H_2O_2$ content of the composition was given as being at least 2%, and preferably 4.5 to 70% by weight. Prolonged drying of the composition, in an attempt to reduce the water content, however, resulted in a substantial loss of $H_2O_2$ from the complex. The product was a brittle, transparent, gummy, amorphous material, and had a variable $H_2O_2$ content ranging from about 3.20 to 18.07% by weight, depending upon the drying times.

The Shiraeff process did not attain commercial success because (1) the product was not a free-flowing powder and thus could not be handled easily; (2) its water and hydrogen peroxide content varied over a wide range; (3) the complex was not stable; and (4) the aqueous process could not be carried out on a commercial scale.

Merianos, in U.S. Pat. Nos. 5,008,093 and 5,066,488, described a process for making free-flowing, substantially anhydrous complexes of PVP and $H_2O_2$ by reacting PVP and a solution of $H_2O_2$ in an anhydrous organic solvent such as ethyl acetate.

Rossberger et al., in German Patent OLS 3,444,552, published Jun. 12, 1986, described a process for making urea peroxyhydrate using a fluidized bed of urea having a particle size of less than 1000 um onto which was sprayed an aqueous solution of concentrated $H_2O_2$. This technique was practical only because urea is a stable, crystalline compound which readily formed a free-flowing powdery complex upon addition of aqueous hydrogen peroxide solutions.

Biss U.S. Pat. No. 5,077,047 describes a process for the production of PVP-$H_2O_2$ products in the form of free-flowing powders in which a fluidized bed of PVP powders was contacted with finely divided droplets of an aqueous $H_2O_2$ solution.

Production of free-flowing complexes of copolymers of vinyl pyrrolidone and a quaternary ammonium monomer complexed with $H_2O_2$ from such amorphous copolymers and aqueous $H_2O_2$, however, has not been easy to achieve commercially because, during production, the copolymer can alter its physical state, and/or retain excess water and/or free $H_2O_2$, even at elevated drying temperatures, resulting in a gummy rather than a free-flowing product.

Accordingly, it is an object of the present invention to provide copolymers of vinyl pyrrolidone and a quaternary ammonium monomer complexed with $H_2O_2$.

Another object of the invention is to provide a fluidized bed process for making such copolymer-$H_2O_2$ products which are free-flowing by contacting a fluidized bed of copolymer powders with a concentrated, aqueous $H_2O_2$ solution under process conditions which favor formation of a free-flowing complex having about 10 to 20% by weight $H_2O_2$ (about a 1:1 molar ratio) without affecting the physical state of the copolymer powders, and simultaneously and/or subsequently removing water from the product.

SUMMARY OF THE INVENTION

These and other objects and features of the invention are accomplished herein by providing vinyl pyrrolidone and a quaternary ammonium monomer complexed with copolymers $H_2O_2$. The products are made in the form of free-flowing powders in which a fluidized bed of the copolymer powders maintained at a reaction temperature of from about ambient temperature to 60° C. which is contacted with finely divided droplets of a 30 to 85% by weight aqueous $H_2O_2$ solution.

In the preferred embodiments of the invention, the bed temperature is maintained at about 35°–50° C., a 50 to 70% aqueous $H_2O_2$ solution is used, and the feed rate for introduction of the $H_2O_2$ solution is about 1–10 g/minute/kg copolymer used, preferably 2–5 g/minute/kg copolymer.

The copolymer-$H_2O_2$ product obtained herein is a free-flowing powder having about 10 to 20% by weight $H_2O_2$ therein, which corresponds approximately to a 1:1 molar ratio of its components, with no excess or free peroxide therein, and having less than about 5% water therein.

The product herein is useful as a hair bleach enhancer which provides dual hair conditioning properties.

DETAILED DESCRIPTION OF THE INVENTION

In accordance with the present invention, a fluidized bed containing a charge of suitable copolymer powders is reacted with an aqueous solution of concentrated hydrogen peroxide. Such copolymers for use herein are copolymers of vinyl pyrrolidone and a quaternary ammonium monomer, which can be made by copolymerizing vinyl pyrrolidone with the quaternary ammonium monomer by solution polymerization in water ethyl alcohol or isopropyl alcohol, or by precipitation polymerization in cyclohexane or heptane, and under conditions which provide high molecular weight copolymers, i.e. about 100,000 to about 2,000,000 Daltons.

Suitable quaternary ammonium monomers for copolymerization with vinyl pyrrolidone include acrylamido, acrylate, vinyl and alkyl quaternary ammonium monomers, in an amount of about 1–30 mole %, preferably 5–15 mole %, of the copolymer. Additional comonomers also may be included in the copolymer, in an amount up to about 10% by weight thereof, and these comonomers are selected from acrylate esters, vinyl amides and vinyl esters.

Representative commercially available quaternary ammonium monomers include the following:

DADMAC—Diallyldimethyl ammonium chloride
DMAEMA(Q)—Dimethylaminoethyl methacrylate, quaternized
DMAEA(Q)—Dimethylaminoethyl acrylate, quaternized
MAPTAC—Methacrylamidopropyltrimethylammonium chloride
DADEAC—Diallyldiethylammonium chloride Preferably, the quaternary ammonium monomer should contain a minimum amount of residual tertiary amine therein, which could react with peroxide and cause instability problems for the complex.

A preferred copolymer for use herein is the copolymer of vinyl pyrrolidone and MAPTAC, known as GAFQUAT® HS-100 resin (International Specialty Products), which is used herein in the form of powders thereof.

The hydrogen peroxide solution used herein usually contains about 30 to 85% hydrogen peroxide. A 50 to 70% $H_2O_2$ solution, however, is preferred because of the inherent danger present in use of the higher $H_2O_2$ concentrations.

The fluidized bed of copolymer powders can be maintained in the fluidized condition by directing a current of dry air through the powders, by mechanical agitation of the powders, or by a combination of both techniques.

The fluidized bed also is maintained at a suitable bed (reaction) temperature at which formation of the desired copolymer-$H_2O_2$ complex product can occur readily without affecting the powdery state of the copolymer, and at which temperature excess water from the $H_2O_2$ solution can be quickly removed both from the product and the copolymer bed itself. The selected bed temperature also will enhance the formation of a free-flowing powder rather than a gum. Such suitable reaction temperatures range from ambient temperature to about 60° C., preferably about 35° to 50° C.

The aqueous, concentrated $H_2O_2$ solution preferably is contacted with the copolymer powders as finely divided droplets of liquid. Such desired droplets may be formed by pumping the $H_2O_2$ solution through a spray nozzle and onto the copolymer bed at a selected rate and for a predetermined period of time. Any spray nozzle capable of producing a fine dispersion of droplets may be used for this purpose. If necessary, however, a stream of air may be introduced into such nozzle with the solution to assist in atomizing the solution into finely divided droplets.

The spray solution of aqueous $H_2O_2$ thus formed preferably is introduced into the fluidized bed of copolymer powders at a selected rate such that excess water can be removed therein during formation of the complex without retaining free $H_2O_2$ therein. A suitable feed rate for introduction of the $H_2O_2$ solution herein is about 1-10 g $H_2O_2$ solution/minute/kg copolymer, preferably about 2-5 g $H_2O_2$ solution/minute/kg copolymer. Under these selected flow rate conditions, a free-flowing powder of the desired copolymer-$H_2O_2$ complex is obtained containing about 10-20% $H_2O_2$, and about 5% or less water therein.

In the preferred form of the process of the invention, the spray solution of $H_2O_2$ is directed onto the copolymer bed for a period sufficient to form a free-flowing powder having an $H_2O_2$ content of about 10 to 20% by weight, which corresponds to a complex having about a 1:1 molar ratio of copolymer to $H_2O_2$ At this point in the process, the feed is discontinued to preclude the formation of excess water and/or free $H_2O_2$ on the free-flowing powder which can cause it to become gummy. The appearance of a gummy product is indicative of the presence of undesired excess water and/or free $H_2O_2$ in the product.

The spray solution of $H_2O_2$ may be directed onto the fluidized bed as a vertical, horizontal or by downward flow of droplets.

If a fluidizing air stream is used to create the fluid bed, it is usually directed upwardly against the copolymer powders. Such air currents also can assist in carrying water away from the bed. An exhaust suction system also may be used to aid in removal of water in the air stream. The fluidized state of the bed also may be maintained using mechanical agitation, or a combination of both air and mechanical means.

The process of the invention can be carried out in one or two steps, i.e. removal of water from the product and bed can take place either (a) simultaneous with, or after mixing, of the reaction components in the same apparatus, or (b) in a downstream drying step, or (c) by a combination of both steps. The particular method of drying will depend upon the type of equipment used. For example, if a fluidized bed mixer is used, such as a plowshare, belt screw or paddle mixer, then the moist copolymer-$H_2O_2$ product can be dried further in a separate dryer. This sequence is characterized as a two-step process. Any suitable dryer can be used for this purpose, such as a vacuum, radiant heat or contact dryer.

Furthermore, if desired, application of the spray $H_2O_2$ solution onto the copolymer bed, followed by downstream drying, may be carried out in several stages in order to increase the $H_2O_2$ content of the product towards the desired 1:1 molar ratio, and to reduce its water content.

Moreover, a fluid bed dryer may be used in the process which has the dual capabilities of providing both the fluidized bed and drying functions. Accordingly, drying of the product will begin and be completed during reaction between the copolymer charge and the aqueous $H_2O_2$ solution. Such a process may be considered as taking place in a one-step.

Preferably, reaction and dehydration are continued until the product reaches a desired $H_2O_2$ content, suitably about 10-20% $H_2O_2O$, with less than about 5% water. Moreover, it is essential that the product remain in the desired free-flowing state after completion of addition of the $H_2O_2$ solution.

The size of the fluidized bed reactor, the rate of addition of the hydrogen peroxide solution, and the reaction times will vary with the particular equipment used, as well as the concentration of the hydrogen peroxide solution and the reaction temperature, keeping in mind the purposes intended to be achieved with respect to each of these process parameters. However, it is believed that the following examples will illustrate the employment of these parameters to provide a process which can be used for the production of the desired copolymer-$H_2O_2$ products. These examples, of course, are given by way of illustration only, and are not to be construed as limiting the invention.

EXAMPLE 1

200 g of a powdered copolymer of GAFQUAT® HS-100 (International Specialty Products), which is the copolymer of 85% vinyl pyrrolidone and 15% 3-methacrylamidopropyl trimethylammonium chloride, was charged into a fluid bed dryer apparatus. Then, with the assistance of an air stream, 80 g. of a 50% aqueous $H_2O_2$ solution was sprayed onto the fluidized bed of the copolymer at the rate of 2 g of the solution/minute/kg copolymer at 50° C. Vacuum was applied during the application of the peroxide solution to remove water from the air stream. The product was a free-flowing powder of the complex of the copolymer and $H_2O_2$, in a yield of 253 g. The peroxide content was 16%; and it contained 5% water.

EXAMPLE 2

The procedure of Example 1 is repeated using equivalent amounts of a copolymer of vinyl pyrrolidone and diallyldimethyl ammonium chloride, quaternized dimethylaminoethyl methacrylate, quaternized dimethylaminoethyl acrylate, and diallyldiethylammonium chloride, optionally, with up to 10% by weight of a comonomer selected from an acrylate ester, vinylamide and a vinylester, with similar results.

The product of the invention can be used where the disinfectant or bleaching property of $H_2O_2$ is desired, and, in a cosmetic composition, the hair conditioning property of the copolymer in the complex provides the dual action of bleaching and conditioning.

While the invention has been described with particular reference to certain embodiments thereof, it will be understood that changes and modifications may be made which are within the skill of the art. Accordingly, it is intended to be bound only by the following claims, in which:

What is claimed is:

1. A process for the production of free-flowing powders of a copolymer of vinyl pyrrolidone and a quaternary ammonium monomer complexed with $H_2O_2$ comprising reacting a fluidized bed of said copolymer maintained at a reaction temperature of from ambient temperature of about 60° C. with finely divided droplets of a 30 to 85% by weight aqueous solution of $H_2O_2$, which is introduced at a rate of about 2-5 g of solution/min/kg copolymer, and drying the product.

2. A process according to claim 1 wherein said solution is introduced at a selected feed rate such that excess water can be removed during formation of said product.

3. A process according to claim 1 wherein said reaction temperature is about 35° to 50° C.

4. A process according to claim 1 wherein a 50 to 70% $H_2O_2$ solution is used.

5. A process according to claim 1 wherein drying is carried out in the fluidized bed during formation of the product, or in a downstream dryer.

6. A process according to claim 5 wherein both said reaction and drying steps are carried out in a fluidized bed dryer.

7. A process according to claim 5 wherein the reaction is carried out in a fluidized bed reactor, and further drying of the wet product is performed in a downstream dryer.

8. A process according to claim 1 wherein air is used to fluidize the copolymer powders and to assist in removing water from the fluidized bed during the process.

9. A process according to claim 1 wherein the product contains about 5% or less water therein.

10. A process according to claim 1 wherein air is used to assist in forming spray droplets of the $H_2O_2$ solution.

11. A process according to claim 1 wherein said monomer is methacrylamidopropyl trimethyl ammonium chloride.

* * * * *